United States Patent
Hobot et al.

(10) Patent No.: US 8,940,315 B2
(45) Date of Patent: Jan. 27, 2015

(54) BENZODIAZEPINE FORMULATION IN A POLYORTHOESTER CARRIER

(75) Inventors: Christopher M. Hobot, Tonka Bay, MN (US); Michael E. Benz, Ramsey, MN (US); Keith R. Hildebrand, Houlton, WI (US); Bryant J. Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1105 days.

(21) Appl. No.: 12/426,031

(22) Filed: Apr. 17, 2009

(65) Prior Publication Data
US 2009/0202604 A1 Aug. 13, 2009

Related U.S. Application Data

(60) Provisional application No. 61/046,201, filed on Apr. 18, 2008, provisional application No. 61/046,213, filed on Apr. 18, 2008.

(51) Int. Cl.
| | |
|---|---|
| A61F 13/00 | (2006.01) |
| A01N 43/62 | (2006.01) |
| A61K 31/55 | (2006.01) |
| A61K 31/197 | (2006.01) |
| A61K 9/00 | (2006.01) |
| A61K 47/34 | (2006.01) |

(52) U.S. Cl.
CPC ............. *A61K 31/197* (2013.01); *A61K 9/0024* (2013.01); *A61K 47/34* (2013.01)
USPC .......................................... 424/422; 514/220

(58) Field of Classification Search
None
See application file for complete search history.

(56) References Cited

U.S. PATENT DOCUMENTS

| | | | |
|---|---|---|---|
| 2,957,856 A | 10/1960 | Guest et al. |
| 3,948,254 A | 4/1976 | Zaffaroni |
| 4,079,038 A | 3/1978 | Choi et al. |
| 4,093,709 A | 6/1978 | Choi et al. |
| 4,131,648 A | 12/1978 | Choi et al. |
| 4,136,252 A | 1/1979 | Capozza |
| 4,138,344 A | 2/1979 | Choi et al. |
| 4,180,646 A | 12/1979 | Choi et al. |
| 4,304,767 A | 12/1981 | Heller et al. |
| 4,389,330 A | 6/1983 | Tice et al. |
| 4,489,056 A | 12/1984 | Himmelstein et al. |
| 4,513,143 A | 4/1985 | Ng et al. |
| 4,532,335 A | 7/1985 | Helwing |
| 4,549,010 A | 10/1985 | Sparer et al. |
| 4,638,045 A | 1/1987 | Kohn et al. |
| 4,639,366 A | 1/1987 | Heller |
| 4,735,804 A | 4/1988 | Caldwell et al. |
| 4,758,436 A | 7/1988 | Caldwell et al. |
| 4,764,364 A | 8/1988 | Heller et al. |
| 4,765,973 A | 8/1988 | Heller |
| 4,767,627 A | 8/1988 | Caldwell et al. |
| 4,780,319 A | 10/1988 | Zentner et al. |
| 4,855,132 A | 8/1989 | Heller et al. |
| 4,898,928 A | 2/1990 | Heller et al. |
| 4,946,931 A | 8/1990 | Heller et al. |
| 4,957,998 A | 9/1990 | Heller et al. |
| 5,013,821 A | 5/1991 | Heller et al. |
| 5,030,457 A | 7/1991 | Ng et al. |
| 5,108,755 A | 4/1992 | Daniels et al. |
| 5,211,951 A | 5/1993 | Sparer et al. |
| 5,254,345 A | 10/1993 | Pogany et al. |
| 5,336,505 A | 8/1994 | Ng et al. |
| 5,374,681 A | 12/1994 | Kroner et al. |
| 5,461,140 A | 10/1995 | Heller et al. |
| 5,487,739 A | 1/1996 | Aebischer et al. |
| 5,587,507 A | 12/1996 | Kohn et al. |
| 5,618,563 A | 4/1997 | Berde et al. |
| 5,700,485 A | 12/1997 | Berde et al. |
| 5,747,058 A | 5/1998 | Tipton et al. |
| 5,747,060 A | 5/1998 | Sackler et al. |
| 5,752,930 A | 5/1998 | Rise et al. |
| 5,801,188 A | 9/1998 | Hassenbusch, III et al. |
| 5,824,343 A | 10/1998 | Ng et al. |
| 5,837,228 A | 11/1998 | Shih et al. |
| 5,919,473 A | 7/1999 | Elkhoury |
| 5,931,809 A | 8/1999 | Gruber et al. |
| 5,939,453 A | 8/1999 | Heller et al. |
| 5,942,241 A | 8/1999 | Chasin et al. |
| 5,968,542 A | 10/1999 | Tipton |
| 5,968,543 A | 10/1999 | Heller et al. |

(Continued)

FOREIGN PATENT DOCUMENTS

| | | |
|---|---|---|
| EP | 0 168 277 B1 | 1/1986 |
| EP | 0 168 277 B2 | 1/1986 |

(Continued)

OTHER PUBLICATIONS

Schmidt et al., in Pediatric Anesthesia 2007, 17, 667-674.*

(Continued)

*Primary Examiner* — Dennis Heyer
*Assistant Examiner* — Daniel M Podgorski
(74) *Attorney, Agent, or Firm* — Sorell Lenna & Schmidt LLP

(57) ABSTRACT

Effective treatments of pain for extended periods of time are provided. The treatments include the administration of one or more drug depots intraspinally wherein the drug depots include an effective amount of a benzodiazepine, such as midazolam, formulated within a polyorthoester. By administration of one or more drug depots, one can relieve pain caused by diverse sources, including but not limited to chronic pelvic pain syndromes, spinal disc herniation (i.e. sciatica), spondilothesis, stenosis, discongenic back pain and joint pain, as well as pain that is incidental to surgery. In some embodiments, the relief can be for at least twenty-five days, at least fifty days, at least one hundred days or at least one hundred and thirty-five days.

18 Claims, No Drawings

(56) References Cited

U.S. PATENT DOCUMENTS

| | | | |
|---|---|---|---|
| 5,980,927 A * | 11/1999 | Nelson et al. | 424/425 |
| 6,001,386 A | 12/1999 | Ashton et al. | |
| 6,007,843 A | 12/1999 | Drizen et al. | |
| 6,096,344 A | 8/2000 | Liu et al. | |
| 6,120,491 A | 9/2000 | Kohn et al. | |
| 6,133,402 A | 10/2000 | Coates et al. | |
| 6,214,370 B1 | 4/2001 | Nelson et al. | |
| 6,214,387 B1 | 4/2001 | Berde et al. | |
| 6,238,702 B1 | 5/2001 | Berde et al. | |
| 6,248,345 B1 | 6/2001 | Goldenheim et al. | |
| 6,368,315 B1 | 4/2002 | Gillis et al. | |
| 6,413,536 B1 | 7/2002 | Gibson et al. | |
| 6,465,458 B1 | 10/2002 | Wong et al. | |
| 6,514,516 B1 | 2/2003 | Chasin et al. | |
| 6,524,606 B1 * | 2/2003 | Ng et al. | 424/425 |
| 6,524,607 B1 | 2/2003 | Goldenheim et al. | |
| 6,534,081 B2 | 3/2003 | Goldenheim et al. | |
| 6,551,290 B1 | 4/2003 | Elsberry et al. | |
| 6,571,125 B2 | 5/2003 | Thompson | |
| 6,594,880 B2 | 7/2003 | Elsberry | |
| 6,601,386 B1 | 8/2003 | Hori et al. | |
| 6,602,975 B2 | 8/2003 | Hubbell et al. | |
| 6,613,355 B2 * | 9/2003 | Ng et al. | 424/425 |
| 6,667,371 B2 | 12/2003 | Ng et al. | |
| 6,699,908 B2 | 3/2004 | Sackler et al. | |
| 6,703,389 B2 | 3/2004 | Wong et al. | |
| 6,790,458 B2 | 9/2004 | Ng et al. | |
| 6,793,938 B2 | 9/2004 | Sankaram | |
| 6,822,000 B2 | 11/2004 | Ng et al. | |
| 6,861,068 B2 | 3/2005 | Ng et al. | |
| 6,863,782 B2 | 3/2005 | Newsome et al. | |
| 6,921,541 B2 | 7/2005 | Chasin et al. | |
| 6,933,328 B2 | 8/2005 | Schacht | |
| 6,946,145 B2 | 9/2005 | Ng et al. | |
| 6,969,383 B2 | 11/2005 | Hildebrand | |
| 6,982,089 B2 | 1/2006 | Tobinick | |
| 7,045,589 B2 | 5/2006 | Heller et al. | |
| 7,163,694 B2 | 1/2007 | Heller et al. | |
| 7,288,609 B1 | 10/2007 | Pacetti | |
| 7,319,132 B2 | 1/2008 | Musa | |
| 2002/0037300 A1 | 3/2002 | Ng et al. | |
| 2002/0114835 A1 | 8/2002 | Sackler et al. | |
| 2002/0176844 A1 | 11/2002 | Ng et al. | |
| 2003/0114394 A1 | 6/2003 | Levine et al. | |
| 2003/0138474 A1 | 7/2003 | Ng et al. | |
| 2003/0152630 A1 | 8/2003 | Ng et al. | |
| 2003/0170288 A1 | 9/2003 | Carr et al. | |
| 2003/0185873 A1 | 10/2003 | Chasin et al. | |
| 2003/0212148 A1 | 11/2003 | Ng et al. | |
| 2004/0001872 A1 | 1/2004 | Shih et al. | |
| 2004/0006070 A1 * | 1/2004 | Hassenbusch et al. | 514/220 |
| 2004/0033251 A1 | 2/2004 | Sparer et al. | |
| 2004/0039437 A1 | 2/2004 | Sparer et al. | |
| 2004/0047911 A1 | 3/2004 | Lyu et al. | |
| 2004/0086569 A1 | 5/2004 | Sparer et al. | |
| 2004/0096506 A1 | 5/2004 | Heller et al. | |
| 2004/0101557 A1 | 5/2004 | Gibson et al. | |
| 2004/0109893 A1 | 6/2004 | Chen et al. | |
| 2004/0115273 A1 | 6/2004 | Sparer et al. | |
| 2004/0126431 A1 | 7/2004 | Largarce et al. | |
| 2004/0127978 A1 | 7/2004 | Sparer et al. | |
| 2004/0146550 A1 | 7/2004 | Ng et al. | |
| 2004/0156907 A1 | 8/2004 | Ng et al. | |
| 2004/0220545 A1 | 11/2004 | Heruth et al. | |
| 2004/0253310 A1 | 12/2004 | Fischer et al. | |
| 2005/0004221 A1 | 1/2005 | Hildebrand et al. | |
| 2005/0025834 A1 | 2/2005 | Guo et al. | |
| 2005/0042194 A1 | 2/2005 | Ng et al. | |
| 2005/0063907 A1 * | 3/2005 | Brandon et al. | 424/9.4 |
| 2005/0064005 A1 | 3/2005 | Dinh et al. | |
| 2005/0064038 A1 | 3/2005 | Dinh et al. | |
| 2005/0074506 A1 | 4/2005 | Natan et al. | |
| 2005/0079202 A1 | 4/2005 | Chen et al. | |
| 2005/0090548 A1 | 4/2005 | Hildebrand et al. | |
| 2005/0090549 A1 | 4/2005 | Hildebrand et al. | |
| 2005/0197341 A1 | 9/2005 | Woolf et al. | |
| 2005/0228451 A1 | 10/2005 | Jaax et al. | |
| 2006/0046961 A1 | 3/2006 | McKay et al. | |
| 2007/0265355 A1 | 11/2007 | Benz et al. | |
| 2008/0033140 A1 | 2/2008 | Alkatout et al. | |
| 2008/0286326 A1 | 11/2008 | Benco | |

FOREIGN PATENT DOCUMENTS

| | | |
|---|---|---|
| EP | 0 202 159 B1 | 11/1986 |
| EP | 0 208 617 B1 | 1/1987 |
| EP | 0 473 223 B1 | 3/1992 |
| EP | 0 102 265 B1 | 7/1992 |
| EP | 0 524 831 A1 | 1/1993 |
| EP | 1 142 596 A1 | 10/2001 |
| EP | 1 225 172 A1 | 7/2002 |
| WO | WO 90/12605 A1 | 11/1990 |
| WO | WO 97/25366 A1 | 7/1997 |
| WO | WO 01/43528 A2 | 6/2001 |
| WO | WO 01/85139 A2 | 11/2001 |
| WO | WO 01/85139 A3 | 11/2001 |
| WO | WO 02/38185 A2 | 5/2002 |
| WO | WO 02/38185 A3 | 5/2002 |
| WO | WO 02/092661 A1 | 11/2002 |
| WO | WO 03/037381 A1 | 5/2003 |
| WO | WO 03/044076 A1 | 5/2003 |
| WO | WO 03/072057 A2 | 9/2003 |
| WO | WO 2005/009408 A2 | 2/2005 |
| WO | WO 2005/009408 A3 | 2/2005 |
| WO | WO 2005/092337 A1 | 10/2005 |
| WO | WO 2005/120435 A2 | 12/2005 |
| WO | WO 2007/133751 A2 | 11/2007 |
| WO | WO 2008/005371 A2 | 1/2008 |

OTHER PUBLICATIONS

Al Malyan et al. in the Journal of Craniofacial Surgery (17,(2) 302-313, 2006).*

Goodman and Gilman's The Pharmacological Basis of Therapeutics (Tenth Edition (2001), McGraw Hill, Chapter I, pp. 3-29.*

Kim et al. (International Journal of Pharmacuetics, 2005, 304, 165-177).*

PCT International Search Report., PCT/US2009/041068, Mailed Nov. 2, 2009.

Anderson et al., "General Acid Catalysis of Ortho Ester Hydrolysis", J. Org. Chem, 37(12):1993-1996, Jun. 16, 1972.

Barr et al., "Post Surgical Pain Management with Poly(ortho esters)", Adv. Drug Deliv. Rev., 54(7):1041-1048, Oct. 16, 2002.

Chiang et al., "Effect of Phenyl Substitution on Ortho Ester Hydrolysis", J.A.C.S., 96(14):4494-4499, Jul. 10, 1974.

Crivello et al., "Ketene Acetal Monomers: Synthesis and Characterization", J. of Polymer Science Part A: Polymer Chem., 34(15):3091-3102, Nov. 15, 1996.

Deng et al., "In Vitro Characterization of Polyorthoester Microparticles Containing Bupivacaine", Pharmaceutical Development and Technology, 8(1):31-38, 2003.

Elbadawi, "Interstitial Cytitis: A Critique of Current Concepts with a New Proposal for Pathologic Diagnosis and Pathogenesis", Urology, 49(5A):14-50, May 1997.

Hansen, "Treatment of Chronic Pain with Antiepileptic Drugs: A New Era.", Sothern Medical Journal, 92(7):642-649, Jul. 1999.

Heller, "Ocular Delivery Using Poly(ortho esters)", Adv. Drug Deliv. Rev., 57(14):2053-2062, Dec. 13, 2005.

Heller et al., "Poly(ortho esters)—From Concept to Reality", Biomacromolecules, 5(5):1625-1632, Jun. 29-Jul. 4, 2003.

Heller et al., "The Effect of Copolymerized 9,10-Dihydroxystaeric Acid on Erosion Rates of Poly(ortho ester) and its Use in the Delivery of Levonorgestrel", J. Controlled Release, 5(2):173-177, Sep. 1987.

Heller et al., "Development of Poly(ortho esters) and their Application for Bovine Serum Albumin and Bupivacaine Delivery", J. Conrtolled Release, 78(1-3):133-141, Jan. 17, 2002.

Heller et al., "Injectable Semi-Solid Poly(ortho esters) for the Controlled Delivery of Therapeutic Agents: Synthesis and Applications", Drug Deliv. Tech., 2(1): 6 pages, Jan./Feb. 2002.

(56) References Cited

OTHER PUBLICATIONS

Heller et al., "Poly(ortho esters)" Synthesis, Characterization, Properties and Uses, Adv. Drug Deliv. Rev., 54(7):1015-1039, Oct. 16, 2002.

Hemmerich, "Polymer Materials Selection for Radiation-Sterililzed Products", Medical Device and Diagnostic Industry Magazine, Part 2:78-89, Feb. 22, 2000.

Irwin et al., "Lumbar Epidural Blockade for Management of Pain in Interstitial Cystitis", British Journal of Urology, 71(4):413-416, 1993.

Kohn et al., "Bioresorbable and Bioerodable Materials,", Biomaterials Science: An Introduction to Materials in Medicine, San Diego CA, Title Page, Copyright Page & pp. 64-72, 1996.

Legarce et al., "Baclofen-Loaded Microspheres: Preparation and Efficacy Testing in a New Rabbit Model", European Journal of Pharmaceutics and Biopharmaceutics, 59:449-459, 2005.

Lyu et al., "Analytical Solutions to Mathematical Models of the Surface and Bulk Erosion of Solid Polymers", J. Polymer Sci., Part B: Polymer Physics, 43(4):383-397, Feb. 15, 2005.

Merkli et al., "Purity and Stability Assessment of a Semi-Solid Poly(ortho ester) Used in Drug Delivery Systems", Biomaterials, 17(9):897-902, May 17, 1996.

Moore et al., "Mechanism of the Alternating Copolymerization of Epoxides and Co2 Using Beta-Dilminate Zinc Catalysts: Evidence for a Bimetallic Epoxide Enchainment", J.A.C.S., 125(39):11911-11924, Oct. 1, 2003.

Ng et al., "Development of a Poly(ortho ester) Prototype with a Latent Acid in the Polymer Backbone for 5_Fluorouracil Delivery", J. of Controlled Release, 65(3):367-374, Apr. 3, 2000.

Ng et al., "Synthesis and Erosion Studies of Self Catalyzed Poly(ortho ester)s", Macromolecules, 30(4):770-772, Feb. 24, 1997.

Ng et al., "Poly (Ortho Esters) by the Addition of Diols to a Diketene Acetal", Macromolecular Synthesis, 11:23-26, 1992.

Nguyen et al., "Some Equilibrium and Kinetic Aspects of Water Sorption in Poly(ortho esters)s", Int'l J. Pharms., 25(1):1-12, Jun. 1985.

Nguyen et al., "Hydrolysis of Some Poly(ortho ester)s in Homogeneous Solutions", J. of Pharmaceutical Sciences, 73(11):1563-1568, Nov. 1984.

Pogany et al., "Gas Chromatographic Assay for 3,9-diethylidene-2,4,8,10-tetraoxaspirol[5,5]undecane,", J. of Chromatography A, 508:179-186, 1990.

Pontari et al., "Mechanisms in Prostatitis/Chronic Pelvic Pain Syndrome", The Journal of Urology, 172:839-845, Sep. 2004.

Potts, "Chronic Pelvic Pain Syndrome: A Non-Prostatocentric Perspective", World J. Urol., 21:54-56, 2003.

Schwach-Abdellaoui et al., "Hydrolysis and Erosion Studies of Autocatalyzed Poly(ortho esters) Containing Lactoyl-Lactyl Acid Dimers", Macromolecules, 32(2):301-307, Jan. 5, 1999.

Schwach-Abdellaoui et al., "Control of Molecular Weight for Auto-Catalyzed Poly(ortho ester) Obtained by Polycondensation Reaction", Int'l J. Polymer Anal. Charact., 7(1-2):145-161, Jan. 2002.

Schwach-Abdellaoui et al., "Synthesis and Characterization of Self-Catalyzed Poly(ortho esters) Based on Decanediol and Decanediol-Lactate", J. Biomater Sci. Polymer Edn., 10(3):375-389, 1999.

Shakesheff et al., "Release of Protein from a Poly(ortho ester) Film During Surface Erosion Studies by in Situ Atomic Force Microscopy", Langmuir, 11(7):2547-2553, Jul. 1995.

Shih, "A Graphical Method for the Determination of the Mode of Hydrolysis of Biodegradable Polymers", Pharm. Research, 12(12):2036-2040, Dec. 1995.

Shih, "Calculation of Hydrolytic Rate Constants of Poly(ortho ester)s from Molecular Weights Determined by Gel Permeation Chromatography", Pharm. Research, 12(12):2041-2048, Dec. 1995.

Sintzel et al., "Synthesis and Characterization of Self-Catalyzed Poly(ortho ester)", Biomaterials, 19(7-9):791-800, Apr.-May 1998.

Wesselmann, "Neurogenic Inflammation and Chronic Pelvic Pain", World J. Urol., 19:180-185, 2001.

Yang et al., "POE-PEG-POE Triblock Copolymeric Microspheres Containing Protein. 1 Preparation and Characterization", J. Controlled Release, 75(1-2):115-128, Jul. 10, 2001.

Zignani et al., "New Generation of Poly(ortho esters): Synthesis, Characterization, Kinetics, Sterilization and Biocompatibility", J. Controlled Release, 48(2):115-129, Oct. 13, 1997.

* cited by examiner

BENZODIAZEPINE FORMULATION IN A POLYORTHOESTER CARRIER

This application claims the benefit of the filing date of U.S. Provisional Application No. 61/046,201 filed Apr. 18, 2008, entitled "Clonidine Formulations in a Biodegradable Polymer Carrier," and U.S. Provisional Application No. 61/046,213 filed Apr. 18, 2008, entitled "Medical Devices and Methods Including Polymers Having Biologically Active Agents Therein," both of which are hereby incorporated by reference thereto.

BACKGROUND

Pain control is of prime importance to anyone treating many different diseases and medical conditions. Proper pain relief imparts significant physiological and psychological benefits to the patient. Not only does effective pain relief mean a smoother more pleasant recovery (e.g., mood, sleep, quality of life, etc.) with earlier discharge from medical/surgical/outpatient facilities, but it may also reduce the probability of the acute pain state progressing to a chronic pain syndrome.

Pain serves an important biological function. It signals the presence of damage or disease within the body and is often accompanied by inflammation (redness, swelling, and/or burning). There are two types of pain based on temporal classification: acute pain and chronic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, chronic pain serves no beneficial purpose. Chronic pain results when pain associated with an injury or infection continues in an area once the injury or infection has resolved. Chronic pain may involve injury and changes to the nervous system which is referred to as neuropathic pain. Chronic pain may also involve persistent activation of physiological or nociceptive pathways if the insult is prolonged such as pain associated with certain types of cancer.

There are many painful diseases or conditions that require proper pain and/or inflammation control, including but not limited to rheumatoid arthritis, osteoarthritis, spinal disc herniation (i.e., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like.

One category of chronic pain is chronic pelvic pain syndromes. Chronic pelvic pain may occur in both men and women of all ages and results from a variety of injuries and disorders. It is a common and debilitating problem that can significantly impair the quality of life of the patient suffering from it. Chronic pelvic pain occurs in the pelvic or lower abdominal region and can last for six months or longer.

In men, chronic pelvic pain may result from chronic idiopathic prostatitis (also referred to as nonbacterial prostatitis or chronic pelvic pain syndrome), chronic bacterial prostatitis or interstitial cystitis where the symptoms typically include in addition to pelvic pain, urinary urgency and frequency, sexual dysfunction and in most cases patients have a hypertonic pelvic floor muscles upon physical examination. The most common treatment for these disorders involves pharmacologic treatments typically orally administered such as antibiotics, anti-inflammatory agents, alpha blockers, anti-spasmodics, analgesics, and muscle relaxants. Alpha blockers have successfully treated symptoms of prostatitis in some patients, although the improvements have been modest and adverse event rates have been significant. Oral muscle relaxants may help decrease pelvic floor tone but often associated with dose-limiting side effects which limit their usefulness.

Other types of chronic pelvic pain experienced by men include chronic testicular pain (CTP), post vasectomy pain, genitofemoral neuralgia and other pain originating from the testicles, groin, or abdomen. The incidence of patients with CTP, also referred to as orchialgia, orchidynia, or chronic scrotal pain, is large and may be caused by on-going inflammation of the testicle (orchitis) or epididymis (epdidymitis), trauma, tumors, hernia, torsion (twisting of the testicle), varicocele, hydrocele, spermatocele polyarteritis nodosa, and previous surgical interventions such as vasectomy and hernia surgery.

Typically, testicle removal and spermatic cord denervation procedures are used to treat CTP. In spermatic cord denervation procedures, nerves in or adjacent to the spermatic cord, i.e., the genitofemoral nerve or sympathetic nerves, are severed or permanently removed. Such procedures may result in permanent and substantial pain relief regardless of the origin of pain. However, severing or removing these nerves may result in loss of sensation in the testicle and/or scrotum, loss of the cremasteric reflex which may cause fertility issues, and even loss of blood flow causing the testicle to die. Therapeutic nerve blocks may also be used to treat CTP, but generally only relieve pain temporarily.

Chronic pelvic pain is also a common medical problem affecting women today. Sources of pain may include injury to nerves resulting from surgical procedures, non-surgical conditions, vulvodynia which can be very debilitating but has no obvious source, and interstitial cystitis (painful bladder syndrome). Surgical procedures that may injure nerves in the pelvic region resulting in pelvic pain may include urological operations in the pelvic area, gynecological surgery, and hysterectomy. Non-surgical conditions which cause pain in women include adhesions, endometriosis, and pelvic congestion. Irritable bowel syndrome may also be considered a chronic pelvic pain condition. Surgical procedures aimed at removing the suspected painful bladder have generally been unsuccessful and often result in worsening of the pain state. This result suggests that the chronic pain state has extended beyond the peripheral organ and may involve central sensitization with the spinal cord that receives sensory input from the peripheral organs.

One known class of pharmaceuticals used to treat pain is opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Although opioids may be used to manage severe episodes of chronic pelvic pain, chronic opioid use may be associated with the development of tolerance leading to the need for higher doses to produce sustained analgesic effects. They may also be associated with addiction.

One class of pharmaceutical agents are benzodiazepines, which act on the central nervous system to produce various levels of sedative-hypnotic, muscle-relaxant, anxiolytic, and anticonvulsant effects. The members of this class function by interacting with various subunits of the $GABA_A$ receptor that regulates the flux of chloride ions across neuronal cell membranes. Benzodiazepines do not directly activate the $GABA_A$ receptors but instead modulate the receptor thereby enhancing the effects of the endogenous agonist, gamma-aminobutyric acid (GABA); GABA is the major inhibitory neurotransmitter in the central nervous system. As a class, benzodiazepines are all lipophilic in the nonionized state. Benzodiazepines are often subcategorized by their duration of effect from ultra-short acting to long-acting agents and are available in oral, intramuscular, intravenous, and rectal formulations. Specific drugs that are members of the benzodiazepine class include alprazolam, chlordiazepoxide, clonazeparn, chlorazepate, diazepam, estazolam, flurazepam, halazepam, lorazepam, midazolam, oxazepam, quazepam, temazepam, and triazilam.

One specific benzodiazepine that is well known to the medical profession is midazolam, which is widely recognized as an ultra short-acting benzodiazepine derivative. It has potent anxiolytic, amnestic, hypnotic, anticonvulsant, skeletal muscle relaxant, and sedative properties. In general, midazolam, also referred to as 8-chloro-6-(2-fluorophenyl)-1-methyl-4H-imidazo[1,5-a][1,4]benzodiazepine ($C_{18}H_{13}ClFN_3$), may be represented by the following chemical structure:

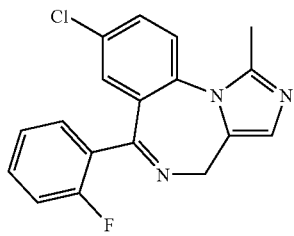 [SMILES: Cc1ncc2n1-c1ccc(Cl)cc1C(c1ccccc1F)=NC2]

Midazolam has been used historically to produce both local and regional anesthesia. Midazolam acts on the benzodiazepine binding site of $GABA_A$ receptors. When bound it enhances the binding of GABA to the $GABA_A$ receptor which results in inhibitory effects on the central nervous system. It can be administered intraspinally (epidural or intrathecal) to treat the spinal cord and provide analgesia for pelvic operations, child delivery, and post surgical recovery. Midazolam is only available as injectable formulations.

There is a need to develop effective formulations of this class of compounds for this application that provide sustained release of benzodiazepines, such as midazolam, thereby provided prolonged pain relief.

SUMMARY

Compositions and methods are provided comprising a benzodiazepine that are administered in order to treat prolonged episodes of pain, such as that associated with chronic pelvic pain conditions. The compositions and methods of the present invention may also for example be used to treat pain due to a spinal disc herniation (i.e., sciatica), spondilothesis, stenosis, osteoarthritis, carpal/tarsal tunnel syndrome, tendonitis, temporomandibular joint disorder (TMJ) and discogenic back pain and joint pain, as well as pain that accompanies or follows surgery.

In one embodiment, an implantable drug depot useful for reducing, preventing or treating pain, such as chronic pelvic pain, in a patient in need of such treatment is provided. The drug depot comprises a polyorthoester ("POE") and a therapeutically effective amount of a benzodiazepine. The drug depot is administered intraspinally to reduce, prevent or treat pain. The drug depot is capable of releasing the benzodiazepine in an amount between 5 and 50 mg per day for a period of 30 to 135 days. The benzodiazepine may be present in an amount of about 1 to about 50 wt. % of the drug depot.

In another embodiment, a pharmaceutical formulation comprising a benzodiazepine, wherein the benzodiazepine comprises from about 1 wt. % to about 50 wt. %, 10 wt. % to about 40 wt. % or about 20 wt. % to about 35 wt. % of the formulation, and a polyorthoester is provided. The pharmaceutical composition may for example, be part of a drug depot. The drug depot may: (i) consist of only the benzodiazepine and the polyorthoester; or (ii) consist essentially of the benzodiazepine and the polyorthoester; or (iii) comprise the benzodiazepine, the polyorthoester and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the drug depot. The drug depot is capable of releasing the benzodiazepine over a period of at least thirty days.

According to another embodiment, there is an implantable drug depot for reducing, preventing or treating chronic pelvic pain in a patient in need of such treatment, the implantable drug depot comprising a benzodiazepine in an amount of from about 1 wt. % to about 50 wt. % of the drug depot and a polyorthoester in an amount of at least 50 wt. % of the drug depot.

In still another embodiment, a method for treating pain, such as chronic pelvic pain, is provided. The method comprises implanting a drug depot intraspinally in an organism to reduce, prevent or treat chronic pelvic pain. The drug depot comprises a benzodiazepine and a polyorthoester. The benzodiazepine is present in an amount from about 1 wt. % to about 50 wt. %, about 10 wt. % to about 40 wt. % or about 20 wt. % to about 35 wt. % of the drug depot.

In still yet another embodiment, an implantable drug depot comprising a therapeutically effective amount of a benzodiazepine and a polyorthoester is provided. The drug depot is capable of releasing an initial bolus dose of the midazolam at a site beneath the skin of a patient, and the drug depot is capable of releasing a sustained release dose of an effective amount of the midazolam over a subsequent period of 30 to 135 days. The benzodiazepine comprises about 1 wt. % to about 50 wt. % of the total wt. % of the drug depot and the polyorthoester comprises at least about 50 wt. % of the drug depot.

In another embodiment, a method of making an implantable drug depot is provided. The method comprises combining a polyorthoester and a therapeutically effective amount of a benzodiazepine and forming an implantable drug depot from the combination.

In various embodiments, the benzodiazepine may be in the form of a base. Alternatively, the benzodiazepine may be in the form of a salt. One example of a salt is a hydrochloride salt. The benzodiazepine may also be in the form of a mixture of a hydrochloride salt and free base.

The drug depot in various embodiments may comprise a hydrophilic agent, such as baclofen, to help control release and/or provide a co-therapeutic effect.

The benzodiazepine in the various embodiments is capable of being released in an amount between 0.25 and 10 mg per day for a period of 30 to 180 days. The drug depot in the various embodiments is capable of releasing about 5% to about 100% of the benzodiazepine relative to a total amount of the benzodiazepine loaded in the drug depot over a period of 30 to 200 days after the drug depot is implanted in the organism.

The benzodiazepine in various embodiments is selected from the group consisting of alprazolam, chlordiazepoxide, clonazepam, chlorazepate, diazepam, estazolam, flurazepam, halazepam, lorazepam, midazolam, oxazepam, quazepam, temazepam, triazilam, and combinations thereof. In some embodiments, the benzodiazepine is medazolam.

The polyorthoester in the various embodiments may comprise about 50 wt. % to about 99 wt. % of the total wt. % of the drug depot. The polyorthoester is capable of degrading or degrades in 200 days or less after the drug depot is implanted at a site.

The drug depot in the various embodiments may further comprise one or more of polyaspirin, polyphosphazene, polyanhydride; polyketal, collagen, starch, pre-gelatinized starch, hyaluronic acid, chitosan, gelatin, alginate, albumin, fibrin, vitamin E analog, d-alpha tocopheryl succinate, poly-ε-caprolactone, dextran, polyvinylpyrrolidone, polyvinyl alcohol, PEGT-PBT copolymer, PEO-PPO-PEO, sucrose acetate isobutyrate, a different polyorthoester or a combination thereof.

The drug depot in various embodiments may comprise a radiographic marker adapted to assist in radiographic imaging. The radiographic marker may comprise barium, bismuth, tantalum, tungsten, iodine, calcium phosphate, and/or metal beads. The drug depot in various embodiments is capable of releasing between 0.25 and 10 milligrams (mg) per day of a benzodiazepine to reduce, prevent or treat chronic pelvic pain.

The target site in the various embodiments comprises the lumbosacral epidural space or at least one muscle, ligament, tendon, cartilage, spinal disc, spinal foraminal space near the spinal nerve root, facet or synovial joint, or spinal canal.

The pain may be associated with pelvic pain such as interstitial cystitis or chronic nobacterial prostatitis, hernia repair, orthopedic or spine surgery or a combination thereof. The surgery may be arthroscopic surgery, an excision of a mass, hernia repair, spinal fusion, thoracic, cervical, or lumbar surgery, pelvic surgery or a combination thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the midazolam is administered to the body. Thus, a drug depot may comprise a physical structure to facilitate implantation and retention in a target site. The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug depot provides a concentration gradient of the therapeutic agent for delivery to the target site.

"Target site" as used herein is used to refer to an area of the body to which the drug is administered. Target sites desirably used with the methods of this invention include specific regions within the spinal canal. As used herein, the term "spinal region" includes the spinal canal (including the spinal cord, intrathecal space, dura, epidural space, etc.), vertebrae, spinal discs, nerve roots, and the ligaments, tendons and muscles in between and surrounding the vertebrae. In one embodiment of the invention, the target site is epidural. In other embodiments the target site is in the intrathecal or peridural spaces of the spinal region. The target sites for the administration of a drug to alleviate pelvic pain in subjects also experiencing bladder or pelvic floor disorders is desirably in the epidural, peridural or intrathecal spaces in the spinal region between the sacrum and/or coccyx, desirably between Co1 and L1, between S5 and S1, between S2 and L1, or between T10 and S4. In one embodiment, the target site is the spinal region that may be accessed through the sacral hiatus or the sacral foramen.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etch), extent and duration of symptoms, concurrent treatments, frequency of treatment and the effect desired. In some embodiments, the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

As used herein, "biodegradable" and "bioerodible" are used interchangeably and are intended to broadly encompass materials including, for example, those that tend to break down upon exposure to physiological environments. Biodegradable and/or bioerodible polymers known in the art include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)); polyanhydrides; polyketals; and poly(orthoesters), "Biocompatible" means that the depot will not cause substantial tissue irritation or necrosis at the target tissue site.

The phrases "sustained release" and "sustain release" (also referred to as extended release or controlled release) are used herein to refer to one or more therapeutic agent(s) that is introduced into the body of a human or other mammal and continuously or continually release an amount of one or more therapeutic agents over a predetermined time period and at a therapeutic level sufficient to achieve a desired therapeutic effect throughout the predetermined time period. Reference to a continuous or continual release is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or action of the drug.

The two types of formulations (sustain release and immediate release) may be used in conjunction. The sustained release and immediate release may be in one or more of the same depots. In various embodiments, the sustained release and immediate release may be part of separate depots. For example, a bolus or immediate release formulation of midazolam may be placed at or near the target site and a sustain release formulation may also be placed at or near the same site. Thus, even after the bolus becomes completely exhausted, the sustain release formulation would continue to provide the active ingredient for the intended tissue.

In various embodiments, the drug depot can be designed to cause an initial burst dose of therapeutic agent within the first twenty-four hours after implantation. "Initial burst" or "burst effect" refers to the release of therapeutic agent from the depot during the first twenty-four hours after the depot comes in contact with a biological fluid (e.g., interstitial fluid, synovial fluid, cerebrospinal fluid, etc.). The "burst effect" is believed to be due to the increased release of therapeutic agent from the depot. In alternative embodiments, the depot is designed to avoid this initial burst effect.

"Treating" or "treatment" of a disease or condition refers to executing a protocol that may include administering one or more drugs to a patient (human, or other mammal), in an effort to alleviate or eliminate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient.

"Localized" delivery includes delivery where one or more drugs are deposited within or near a tissue, for example, a nerve root of the nervous system or a region of the spinal cord, or in close proximity (within about 0.1 cm, or preferably within about 1.0 cm, for example) thereto.

The term "mammal" refers to organisms from the taxonomic class "mammalia," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate" refers to the percentage of active ingredient that is released over fixed units of time, e.g., mcg/hr, mcg/day, 10% per day for ten days, etc. As persons of ordinary skill know, a release rate profile may, but need not, be linear. By way of a non-limiting example, the drug depot may be a ribbon-like fiber that releases the midazolam over a period of time.

The term "solid" is intended to mean a rigid material, while, "semi-solid" is intended to mean a material that has some degree of flexibility, thereby allowing the depot to bend and conform to the surrounding tissue requirements.

The term "gel" is intended to mean a semi-solid material that may be flowable upon application to the target site, then may harden or increase in viscosity upon delivery.

"Targeted delivery system" provides delivery of one or more drug depots, gels or depots dispersed in the gel having a quantity of therapeutic agent that can be deposited at or near the target site as needed for treatment of pain, inflammation or other disease or condition.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Benzodiazepine

In various embodiments, the benzodiazepine is selected from the group consisting of alprazolam, chlordiazepoxide, clonazepam, chlorazepate, diazepam, estazolam, flurazepam, halazepam, lorazepam, midazolam, oxazepam, quazepam, temazepam, triazilam, and combinations thereof. In some embodiments, the benzodiazepine is midazolam.

When referring to benzodiazepines, such as midazolam, the active ingredient may be in the salt form or the base form (e.g., free base). In various embodiments, if it is in the base form, it may be combined with a polymer such as a polyorthoester under conditions in which there is not significant polymer degradation. By way of a non-limiting example, when formulating a benzodiazepine, such as midazolam, with a polyorthoester, it may be desirable to use the base formulation.

Further, the benzodiazepine, such as midazolam, may be in the salt form and one well-known commercially available salt for midazolam is its hydrochloride salt. Some other examples of potentially pharmaceutically acceptable salts include those salt-forming acids that do not substantially increase the toxicity of a compound, such as, salts of mineral acids such as hydriodic, hydrobromic, phosphoric, metaphosphoric, nitric and sulfuric acids, as well as salts of organic acids such as tartaric, acetic, citric, malic, benzoic, glycolic, gluconic, gulonic, succinic, arylsulfonic, e.g., p-toluenesulfonic acids, and the like.

The benzodiazepine may also be administered with other suitable analgesic agents that include, but are not limited to, acetaminophen, clonidine, bupivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, and nonopioid analgesics such as flupirtine, amitriptyline, carbamazepine, gabapentin, pregabalin, or a combination thereof.

The benzodiazepine, such as midazolam, may also be administered with non-active ingredients. These non-active ingredients may have multi-functional purposes including the carrying, stabilizing and controlling of the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with bupivacaine in addition to the biodegradable polymer include but are not limited to MgO, PEG, MPEG, Span-65, Span-85, pluronic F127, TBO-Ac, sorbital, cyclodextrin, maltodextrin, maltose, mannitol, pluronic F68, $CaCl_2$, and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.1 wt. % to about 10 wt. % of the formulation. In some embodiments, the excipients comprise from about 0.001 wt. % to about 2 wt. % of the formulation. In some embodiments, the excipients comprise from about 0.1 wt. % to about 5 wt. % of the formulation. In some embodiments, the excipients comprise from about 0.1 wt. % to about 2 wt. % of the formulation.

In various embodiments, the depot may comprise a biodegradeable polyorthoester. The mechanism of the degradation process of the polyorthoester can be hydrolytic. In various embodiments, the degradation can occur either at the surface (heterogeneous or surface erosion) or uniformly throughout the drug delivery system depot (homogeneous or bulk erosion). Polyorthoester materials can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties. Some exemplary polyorthoester materials suitable for use in the present invention are described in U.S. patent Application Publication Number 2008/0033140, entitled "Poly(Orthoester) Polymers, and Methods of Making and Using Same" which is hereby incorporated by reference in its entirety.

In some embodiments, the drug depot may not be completely biodegradable. For example, the drug depot may comprise polyorthoester and one of more of the following: polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In various embodiments, the depot may comprise a bioerodable, a bioabsorbable, and/or a biodegradable biopolymer in addition to a polyorthoester that may provide immediate release, or sustained release of the benzodiazepine. The biopolymer may also include one or more of the following biopolymers: polyaspirins, polyphosphazenes, polyanhydrides; polyketals, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, poly-ε-caprolactone, dextrans, polyvinylpyrrolidone, polyvinyl alcohol (PVA), PEGT-PBT copolymer (PolyActive®), PEO-PPO-PEO (Pluronics®), Poloxamer 407, SAIB (sucrose acetate isobutyrate), a different polyorthoester or other biodegradeable polymer or combinations thereof. As persons of ordinary skill are aware, MPEG may be used as a plasticizer for a POE, but other polymers/excipients may be used to achieve the same effect. mPEG imparts malleability to the resulting formulations.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide, sodium phosphate, magnesium oxide or magnesium carbonate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be of different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In some embodiments, the shape and size of the system should be selected so as to minimize or prevent the drug depot from moving after implantation or injection. In various embodiments, the drug depot can be shaped like a sphere, a pellet, a cylinder such as a rod or fiber, a flat surface such as a disc, film or sheet (e.g., ribbon-like) or the like. Flexibility may be a consideration so as to facilitate placement of the drug depot. In one embodiment, the drug depot has the shape of a ribbon and has a length of from about 10 mm to 200 mm. In another embodiment, the drug depot is in the form of microspheres having an average diameter from about 1 micron to about 500 microns, more specifically from about 1 micron to about 250 microns, more specifically, from about 1 micron to about 150 microns, and more specifically from about 10 microns to about 100 microns.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium phosphate, and/or metal beads or particles. In various embodiments, the radiographic marker could be a spherical shape or a ring around the depot.

In some embodiments, the drug depot has pores that control release of the drug from the depot. The pores allow fluid into the depot to displace and/or dissolve the drug.

Gel

In various embodiments, midazolam and polyorthoester are administered with or in a gel. The gel may have a pre-dosed viscosity in the range of about 1 to about 200,000 centipoise (cP), 100 to about 20,000 cP, or 500 to about 10,000 cP. After the gel is administered to the target site, the viscosity of the gel will increase and the gel will have a modulus of elasticity (Young's modulus) in the range of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

The gel may be of any suitable type, as previously indicated, and should be sufficiently viscous so as to prevent the gel from migrating from the targeted delivery site once deployed; the gel should, in effect, "stick" or adhere to the targeted tissue site or conform to the target tissue space. The gel may, for example, solidify upon contact with the targeted tissue or after deployment from a targeted delivery system. The targeted delivery system may be, for example, a syringe, a catheter, sheath, needle or cannula or any other suitable device. The targeted delivery system may inject the gel into or on the targeted site. The therapeutic agent may be mixed into the gel prior to the gel being deployed at the targeted site. In various embodiments, the gel may be part of a two-component delivery system and when the two components are mixed, a chemical process is activated to form the gel and cause it to stick or to adhere to the target site.

The gel may harden or stiffen after delivery. Typically, hardening gel formulations may have a pre-dosed modulus of elasticity in the range of about $1\times10^2$ to about $3\times10^5$ dynes/cm$^2$, or $2\times10^2$ to about $2\times10^5$ dynes/cm$^2$, or $5\times10^2$ to about $1\times10^5$ dynes/cm$^2$. The post-dosed hardening gels (after delivery) may have a rubbery consistency and have a modulus of elasticity in the range of about $1\times10^4$ to about $2\times10^5$ dynes/cm$^2$, or $1\times10^5$ to about $7\times10^5$ dynes/cm$^2$, or $2\times10^5$ to about $5\times10^5$ dynes/cm$^2$.

If the gel includes the benzodiazepine, such as midazolam, and a polyorthoester, the polyorthoester concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the target site.

The percentage of polyorthoester present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polyorthoester comprises 20 wt. % to 90 wt. % of the formulation.

In various embodiments, the molecular weight of the polymers that make up the gel can be varied by many methods known in the art. The choice of method to vary molecular weight is typically determined by the composition of the gel (e.g., polymer, versus non-polymer). For example, in various embodiments, the degree of polymerization can be controlled by varying the amount of polymer initiators (e.g. benzoyl peroxide), organic solvents or activator (e.g. DMPT), crosslinking agents, polymerization agent, reaction time and/or by including chain transfer or chain terminating agents.

The gel can vary from low viscosity, similar to that of water, to high viscosity, similar to that of a paste, depending on the molecular weight and concentration of the polyorthoester used in the gel. The viscosity of the gel can be varied such that the composition can be applied to a patient's tissues by any convenient technique, for example, by brushing, dripping, injecting, or painting. Different viscosities of the gel are selected to conform to the technique used to deliver the composition.

The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, NiPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

Drug Delivery

It will be appreciated by those with skill in the art that the depot can be administered to the target site using a catheter or a "cannula", "trocar" or "needle" that can be a part of a drug delivery device e.g., a syringe, a gun drug delivery device, or any medical device suitable for the application of a drug to a targeted site. The catheter, cannula, trocar or needle of the drug depot device is designed to cause minimal physical and psychological trauma to the patient.

Catheters, cannulas, trocars or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The diameter of the cannula or needle will also depend on the site of implantation. In various embodiments, the diameter includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments, the gauge of the needle or cannula is about 18 to about 22 gauge. In some embodiments, the needle or cannula may include two lumens; one for administering the drug depot and a second for administering a radiocontrast agent. This allows both to be administered without having to reposition the needle.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, gold, calcium, and/or metal beads or particles.

In various embodiments, the needle or cannula may include a transparent or translucent portion that can be visualized by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility.

In one embodiment, the drug depot is desirably delivered to the lumbosacral spinal region. A depot may be delivered to that space via a drug delivery catheter. The techniques for such delivery method are well known in the art. In one embodiment, the Seldinger technique is used and an introducer having a lumen is used to enter the spinal space through one of the sacral hiatuses or sacral foramina, a guidewire is passed through the introducer, the introducer is removed and the catheter is advanced over the wire until it is in position for drug delivery.

In various embodiments, to administer the gel having the drug depot dispersed therein to the desired site, first the cannula or needle can be inserted through the skin and soft tissue down to the target site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

The formulations of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatin, lactose, starches, stearic acid, magnesium stearate, talc, vegetable oils, benzyl alcohols, gums, waxes, propylene glycol, polyalkylene glycols and other known carriers for medicaments.

In some embodiments, the benzodiazepine and polyorthoester formulations are suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiskally, peridiskally, epidurally, perispinally, intraarticular injection or combinations thereof. In some embodiments, the injection is intrathecal, which refers to an injection into the spinal canal (subarachnoid space surrounding the spinal cord).

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing a solvent and a biocompatible polymer are combined and placed in a mold of the desired size and shape. In this way, polymeric regions, including barrier layers, lubricious layers, and so forth can be formed. If desired, the solution can further comprise, one or more of the following: the benzodiazepine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming a depot or portions thereof include molding techniques (for example, injection molding, rotational molding, and so forth), extrusion techniques (for example, extrusion, co-extrusion, multilayer extrusion, and so forth) and casting.

Thermoplastic processing in accordance with various embodiments comprises mixing or compounding, in one or more stages, the polyorthoester and one or more of the following: the benzodiazepine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, the benzodiazepine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding a polyorthoester with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the various additives and a polyorthoester may be premixed prior to a final thermoplastic mixing and shaping process, if desired (e.g., to prevent substantial degradation of the therapeutic agent among other reasons).

For example, in various embodiments, a polyorthoester is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the benzodiazepine containing drug depot. Conversely, in another embodiment, the polyorthoester can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the polyorthoester and therapeutic agent and other additives will depend on a number of factors including, for example, the additive(s) used, as well as the type of mixing device used.

In other embodiments, a polyorthoester and one or more therapeutic agents are premixed using non-thermoplastic techniques. For example, the polyorthoester can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing polymer matrix (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the polymer matrix. As above, the resulting solid material can then be granulated for further processing, if desired.

Typically, an extrusion process may be used to form the drug depot comprising a polyorthoester, therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as midazolam is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polyorthoester and then molding the depot to the desired shape. In various embodiments, the benzodiazepine is used and mixed or sprayed with a polyorthoester, and the resulting depot may be formed by extrusion and dried.

In various embodiments, there is a pharmaceutical formulation comprising: a benzodiazepine, wherein the benzodiazepine comprises from about 0.1 wt. % to about 70 wt. % of the formulation, and at least a polyorthoester. In some embodiments, the benzodiazepine comprises from about 1 wt. % to about 50 wt. %, about 5 wt. % to about 50 wt. %, about 5 wt. % to about 40 wt. % or about 10 wt. % to about 35 wt. % of the formulation. In some embodiments, the polyorthoester comprises from about 30 wt. % to about 99.9 wt. %, from about 50 wt. % to about 99 wt. %, from about 50 wt. % to about 95 wt. %, from about 60 wt. % to about 95 wt. %, or from about 65 wt. % to about 90 wt. % of the formulation.

In various embodiments, the drug is present in the depot in the form of a particle and the particle size is from about 0.1 to 1,000 microns in diameter, however, in various embodiments ranges from about 1 micron to 250 microns, or 5 microns to 50 microns in diameter may be used. In some embodiments, the polyorthoester comprises at least 30 wt. %, at least 40 wt. %, at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 99 wt. % of the formulation. It should be noted that particle size may be altered by techniques such as mortar and pestle, grinding, spray drying, jet-drying or jet milling.

In some embodiments, at least 75% of the drug particles have a size from about 1 micron to about 200 microns in diameter, more specifically from about 5 microns to about 50 microns in diameter. In some embodiments, at least 85% of the particles have a size from about 1 micron to about 200 microns in diameter, more specifically from about 5 microns to about 50 microns in diameter. In some embodiments, at least 95% of the particles have a size from about 1 micron to about 200 microns in diameter, more specifically from about 5 microns to about 50 microns in diameter. In some embodiments, all of the particles have a size from about 1 micron to about 200 microns in diameter, more specifically from about 5 microns to about 50 microns in diameter.

In some embodiments, there is a pharmaceutical formulation comprising: a benzodiazepine, and comprises from about 0.1 wt. % to about 70 wt. % of the formulation, and at least a polyorthoester, wherein the polyorthoester comprises at least 30 wt. % of the formulation. In some embodiments, there is a pharmaceutical formulation comprising: a benzodiazepine, wherein a portion of the benzodiazepine is in the form of a salt, such as a hydrochloride salt, and a portion is in the form of a benzodiazepine base, and the mixture comprises about 0.1 wt. % to about 70 wt. % of the formulation, and at least a polyorthoester, wherein the polyorthoester comprises at least 30 wt. % of the formulation.

In some embodiments, there are methods for treating pain, such as chronic pelvic pain. These methods comprise: administering a pharmaceutical composition to an organism, wherein the pharmaceutical composition comprises from about 0.1 wt. % to about 99 wt. % of the formulation comprising at least a polyorthoester and a benzodiazepine. In some embodiments, the loading is from about 5 wt. % to about 95 wt. %. In some embodiments, the loading is from about 10 wt. % to about 90 wt. %. In some embodiments, the loading is from about 20 wt. % to about 80 wt. %.

In some embodiments, the formulations are rigid or slightly rigid with varying length, widths, diameters, etc. For example, certain formulations may have a diameter of between about 0.5-3 mm and a length of about 50-100 mm.

In some embodiments, the benzodiazepine, such as midazolam, is released at a rate of 0.25 mg-10 mg per day for a period of at least thirty days. In some embodiments, this release rate continues for, at least forty days, at least sixty days, at least ninety days, at least one hundred days, at least one-hundred and thirty-five days, at least one-hundred and fifty days, or at least one hundred and eighty days. For some embodiments, 7.5-1,800 milligrams of the benzodiazepine as formulated with a polyorthoester are implanted into a person at or near a target site. It is important to limit the total daily dosage released to an amount less than that which would be harmful to the organism.

The dosage may be from approximately 0.25 to approximately 10 mg/day. Additional dosages of midazolam include from approximately 0.5 mg/day to approximately 8 mg/day, from approximately 1 mg/day to approximately 8 mg/day, and from approximately 1 mg/day to approximately 5 mg/day.

In one exemplary dosing regimen, a rat may be provided with sufficient midazolam in a biodegradable POE polymer to provide sustained release of 10 μg/day midazolam for 90 days. The total amount of midazolam that is administered over this time period would be approximately 900 μg. In another exemplary dosing regimen, a human is provided with sufficient midazolam in a biodegradable POE polymer to provide sustained release of 10 mg/day midazolam for 90 days. The total amount of midazolam that is administered over this time period would be approximately 900 mg.

Having now generally described the invention, the same may be more readily understood through the following reference to the following examples, which are provided by way of illustration and are not intended to limit the present invention unless specified.

EXAMPLES

Example 1

Preparation of Polyorthoester

A polyorthoester having a molecular weight of 133 kDaltons was synthesized by combining a stoichiometric mixture of 3,9-diethylidene-2,4,8,10-tetraoxospiro[5,5]undecane (DETOSU) with a mixture of diols including trans-1,4-cyclohexanedimethanol (54 mole %), 1,6-hexanediol (45 mole %) and diethyl-tartrate (1 mole %). Midazolam was purchased from Orgamol (Switzerland). Methanol and acetone were purchased from Sigma-Aldrich.

Methods: The following compositions were used to prepare a polyothoester: DETOSU at 34.9998 g (164.90 mmole), Trans-cyclohexanedimethanol at 12.5898 g (87.30 mmole), 1,6-hexanediol at 8.5965 g (72.75 mmole), Diethyltartrate at 0.3333 g (1.62 mmole), Para-toluenesulfonicacid at 2325 μl of a 1% (w/v) solution in tetrahydrofuran (THF) and 315 ml of Tetrahydrofuran. In particular, a 1000 ml round bottomed flask was pyro-cleaned, washed with soap and water, then rinsed with acetone, isopropanol, 0.1N NaOH and deionized water, and then oven-dried. All spatulas to be used for preparing the polymer were washed and dried in the oven for at least 2 hours. A small glass beaker was also washed and dried in the oven. All of the reactants were weighed in a beaker. In a $N_2$ glove box, DETOSU was first weighed into the beaker followed by the diols. 200 ml of THF was then added to dissolve the solids and this solution was poured into the round bottomed flask. The rest of the THF was then added to the beaker again and then into the flask. The solution was allowed to stir for 30 minutes. A 1% PTSA catalyst was then added to the solution at which point the solution exothermed vigorously and became very thick. The stirring was then stopped and the solution remained in the flask overnight. An IR scan of a sample of the polymer solution was taken the next day and it showed that the polymerizaion was complete (there was a minor peak at 3501 $cm^{-1}$ but that was due to the thickness of the sample on the IR plate).

A blender was washed and dried in the oven for at least 8 hours. A tweezer was also dried. In the $N_2$ glove box, ~500 ml of anhydrous methanol was added to the blender. Four (4) drops of triethylanine were then added to the waring blender. The polymer solution was then slowly poured into a methanol solution. The polymer precipitated out easily. The precipitated polymer was then redissolved in minimal THF and poured in fresh methanol. The polymer precipitated again and was then put in a mylar boat and dried in the vacuum oven at fill vacuum and 50° C. for two days. The POE polymer was then transferred to a dried jar.

Example 2

Preparation of POE-Midazolam Microspheres

In some embodiments it may be desirable to make drug depots in the form of microspheres. This can be accomplished using methods and apparatus known to those of skill in the art and described herein.

For example, microspheres are prepared using a water/oil emulsion with a vacuum-controlled hardening step. 850 mg of the polymer from Example 1, polyorthoester (54 mole % trans-cylcohexanedimethanol, 45% 1,6-hexanediol and 1% diethyltartrate) is dissolved in methylene chloride along with midazolam (150-mg) at a solids concentration of 1-g per 12-ml. The solution is then filtered through a 0.2 μm PTFE syringe filter. The polymer/drug solution, 12-ml, is added slowly over 1 minute into a 120-ml jar containing 60-ml of a 10 mM Trizma® base buffer at pH 8.5 with 1% (w/v) polyvinylalcohol (Sigma-Aldrich) while being mixed at 6,000 rpm with an IKA Ultra-Turrax T-18 high-shear mixer. The solution is mixed for 2 minutes and then poured into a 250-ml round bottom flask, followed by 20-ml of water used to rinse the jar. The flask is immediately placed on a rotoevaporator and the pressure is reduced from 700 mbar to 5 mbar over 45 minutes and held at 5 mbar for 15 minutes. The hardened microsphere suspension is poured into two 50-ml conical tubes and centrifuged at 1000 rpm for 2 minutes. The supernatant is poured off and the spheres from each tube are transferred to a single 50-ml conical tube and rinsed with 45-ml of water, centrifuged again, and the supernatant is poured off. This is repeated 2 more times and the spheres are then resuspended in 7-ml of water and frozen in liquid nitrogen. The frozen suspension is lyophilized for 24 hours and then transferred to a vacuum oven at 25° C. and dried for 1 week. The microspheres mean particle size is measured with a Horiba LA-950 particle size analyzer.

Example 3

In-vitro Release of Midazolam

Drug elution of midazolam from the microspheres described in Example 2 is measured using a pouch method. The pouch method involves adding 15-mg of the spheres described in Example 2 to a ¾" by ¾" nylon pouch with a 5-micron mesh size. The pouch is prepared by heating sealing 3 sides of the nylon mesh, adding the spheres, and then heat sealing the final side of the pouch. The pouch is placed in 10-ml of phosphate buffered saline pH 7.4 contained in a vial and placed in an incubator/shaker at 37° C. and 100 RPM. Sampling is performed by removing 8-ml of media with a pipette and then adding 8-ml of fresh media to the vial. The samples are then returned to the incubator/shaker. Sampling is performed daily for the first week and then once per week for 180 days. Drug concentrations in the elution media are measured by HPLC with UV detection.

Example 4

Preparation of Spray Dried Midazolam

In some embodiments, the midazolam is formulated with the POE as a particle. It may be desired to have the particles within a desired size range. This can be accomplished by dissolving the midazolam in an appropriate solvent and spray drying the solution using methods and apparatus known to those of skill in the art and described herein.

For example, midazolam is dissolved in methylene chloride to yield a solution. The solution is spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). Exemplary processing parameters include: inlet temp. (40° C.), aspirator (80%), nitrogen inlet (50 mm), spray flow rate (80 mL/hr) and ultrasonic generator (0.8 watts). The spray dried powder is collected and dried, such as for an additional 24 hours at 70° C. and 15 mmHg vacuum.

Example 5

Preparation of Melt Extruded Rods

In some embodiments, the midazolam is melt extruded with the POE. This can be accomplished by using methods and apparatus known to those of skill in the art and described herein.

For example, several formulations having midazolam drug loadings of 5% (w/w), 10% (w/w), 20% (w/w), 30% (w/w), 40% (w/w) and 50% (w/w) are prepared for melt extrusion with POE described in Example 1. Each formulation contains POE polymer ground into powder using a Retsch (Retsch GmbH, Germany) rotor mill with an 80 micrometer sieve filter and spray dried midazolam as described in Example 4. All formulations are dry mixed with a spatula prior to being fed into a Haake Mini-Lab twin screw extruder (Thermo Fischer Scientific, Waltham, Mass.) set at 120° C. and 30 RPM. The rods are extruded out of a 0.75 mm diameter die and pulled by hand to obtain a final diameter of ~0.7-0.8 mm.

The rods are then cut with a razor blade to desired length depending on the corresponding drug loadings. Pellets from each formulation are placed in 20 mL scintillation vials for drug elution testing. In-vitro elution studies are carried out at 37° C. in phosphate-buffered saline (PBS, pH 7.4). In particular, the pellets are incubated in 5 mL of phosphate buffered saline pH 7.4 (Hyclone, 0.0067M) at 37° C. under mild agitation. At pre-selected times over a 135 day period, the buffer is removed for analysis and replaced with fresh buffer medium. The drug content is quantified at 220 nm by a Molecular Devices SpectraMax M2 (Sunnyvale, Calif.) plate reader.

Example 6

Preparation of Spray Dried POE-Midazolam Microparticles

In some embodiments, the midazolam and POE are spray dried together to form microparticles. This can be accomplished using methods and apparatus known to those of skill in the art and described herein.

For example, midazolam and POE are dissolved together in methylene chloride to yield a solution. The solution is spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). Exemplary processing parameters include: inlet temp. (40° C.), aspirator (80%), nitrogen inlet (50 mm), spray flow rate (80 mL/hr) and ultrasonic generator (0.8 watts). The spray dried powder is collected and dried, such as for an additional 24 hours at 70° C. and 15 mmHg vacuum.

Example 7

Epidural Administration of POE-Midazolam Depot in a Rat Model of Bladder Pain

In some embodiments, the drug depot is implanted in a mammal. This can be accomplished by using methods and apparatus known to those of skill in the art and described herein.

For example, an animal model that has been used frequently to study pelvic pain conditions is a rat model of bladder pain. In this model, a female rat is lightly anesthetized with isoflurane and a transurethral catheter is placed into the bladder. The catheter is connected to a pressure transducer so that the pressure within the bladder can be continuously monitored and recorded over time. Fluid is continuously infused into the bladder using a syringe pump at a rate of 0.1 mL/min to cause the bladder to contract repeatedly each time it become fill. This is referred to as a volume-evoked micturition reflex or contraction. A repeated series of bladder contractions (pressure spikes) over time is collected using this method. To mimic normal bladder activity, 0.9% saline is infused into the bladder; to mimic painful bladder activity, a dilute solution of acetic acid (0.5%) is infused into the bladder. Acetic acid infusion produces a marked increase in the frequency of bladder contractions. In human patients that suffer from interstitial cystitis, a common form of pelvic pain, increased frequency of urination and urinary urgency are common clinical symptoms.

In order to evaluate the effects of epidurally administered drugs on normal and painful bladder activity (frequency of reflex bladder contractions), midazolam is continuously administered via an epidural drug depot.

For example, a drug depot designed to deliver 10 µg/day of midazolam is epidurally administered to the mid-lumbar epidural space. The baseline bladder activity is measured before implanting the epidural drug depot, the drug depot system is implanted on day 0 and cystometrograms are recorded periodically over 135 days during which midazolam (25 µg/day) is released into the lumbar epidural space.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for reducing or treating pain in a patient in need of such treatment, the drug depot comprising a polyorthoester in an amount of about 95 to 99 wt % based on the total weight of the drug depot, and mPEG, the drug depot comprising a gel and having a viscosity of about 500 to 10,000 centipoises and a benzodiazepine in an amount of about 1 to 5 wt. % based on the total weight of the drug depot and having a particle size of between about 5 µm to 50 µm the drug depot adapted to be administered intraspinally in the patient to reduce or treat pain, wherein the drug depot is capable of releasing benzodiazepine for a period of at least 30 days after administration.

2. An implantable drug depot according to claim 1, wherein the benzodiazepine is midazolam.

3. An implantable drug depot according to claim 1, wherein the benzodiazepine is capable of being released for a period of 30 to 135 days after administration.

4. An implantable drug depot according to claim 1, wherein the depot further comprises a radiographic marker.

5. An implantable drug depot according to claim 1, further comprising one or more of polyaspirin, polyphosphazene, polyanhydride polyketal, collagen starch, pre-gelatinized starch, hyaluronic acid, chitosan , gelatin, alginate, albumin, fibrin, vitamin E analog, d-alpha tocopheryl succinate, poly-epsilon caprolactone, dextran, polyvinylpyrrolidone, polyvinyl alcohol PEGT-PBT copolymer, PEO-PPO-PEO, sucrose acetate isobutyrate, a different polyorthoester or a combination thereof.

6. An implantable drug depot according to claim 1, wherein the benzodiazepine is in the form of a hydrochloride salt or a mixture of hydrochloride salt and free base.

7. An implantable drug depot according to claim 1 , wherein the drug depot is in the form of a ribbon.

8. An implantable drug depot according to claim 1, wherein the drug depot has a modulus of elasticity in the range of about $2 \times 10^4$ to about $5 \times 10^5$ dynes/cm$^2$.

9. An implantable drug depot according to claim 1, wherein the drug depot releases about 0.25 mg to about 10 mg of the benzodiazepine over a period of 30 days.

10. A method for treating pain, wherein the method comprises implanting a drug depot of claim 1 intraspinally in an organism to reduce or treat pain.

11. A method according to claim 10, wherein the benzodiazepine is midazolam.

12. A method according to claim 10, wherein the midazolam is released in an amount between 0.25 and 10 mg per day for a period of 30 to 135 days.

13. A method according to claim 10, wherein the drug depot is a ribbon.

14. A method according to claim 10, wherein the polyorthoester comprises at least 70 wt. % of the drug depot.

15. A method according to claim 10, wherein the depot is in the form of microspheres having an average diameter from about 1 micron to about 500 microns.

16. A method according to claim 10, wherein the benzodiazepine is present in the depot in the form of particles, wherein at least 75% of the particles have a size from about 5 microns to about 50 microns in diameter.

17. A method according to claim 10, wherein the drug depot further comprises a radiographic marker.

18. A method of making an implantable drug depot of claim 1, the method comprising combining a polyorthoester and a benzodiazepine and forming the implantable drug depot from the combination.

* * * * *